US006681769B2

(12) United States Patent
Sprinkel, Jr. et al.

(10) Patent No.: US 6,681,769 B2
(45) Date of Patent: Jan. 27, 2004

(54) AEROSOL GENERATOR HAVING A MULTIPLE PATH HEATER ARRANGEMENT AND METHOD OF USE THEREOF

(75) Inventors: F. Murphy Sprinkel, Jr., Glen Allen, VA (US); Walter A. Nichols, Chesterfield, VA (US)

(73) Assignee: Crysalis Technologies Incorporated, Richmond, VA (US); .

( * ) Notice: Subject to any disclaimer, the term of this patent is extended or adjusted under 35 U.S.C. 154(b) by 9 days.

(21) Appl. No.: 10/003,438

(22) Filed: Dec. 6, 2001

(65) Prior Publication Data

US 2003/0106552 A1 Jun. 12, 2003

(51) Int. Cl.[7] ........................ A61M 16/00; F23D 11/00; F23D 14/00

(52) U.S. Cl. ............................ 128/203.26; 128/203.12; 128/203.17; 128/203.15; 128/204.17

(58) Field of Search ................................ 261/154, 130, 261/104, 107, DIG. 65; 128/203.13, 203.15, 203.17, 203.26, 203.27, 203.28, 204.17; 392/386, 387, 394, 396, 397, 398

(56) References Cited

U.S. PATENT DOCUMENTS

| | | | |
|---|---|---|---|
| 2,896,856 A | | 7/1959 | Kravits |
| 3,084,698 A | | 4/1963 | Smith |
| 3,157,179 A | | 11/1964 | Paullus et al. |
| 3,162,324 A | | 12/1964 | Houser |
| 3,431,393 A | | 3/1969 | Katsuda |
| 3,486,663 A | | 12/1969 | Humphrey |
| 3,658,059 A | | 4/1972 | Steil |
| 3,716,416 A | * | 2/1973 | Adlhart et al. |
| 3,750,961 A | | 8/1973 | Franz |
| 3,847,304 A | | 11/1974 | Cohen |
| 3,859,398 A | | 1/1975 | Havstad |
| 3,902,635 A | | 9/1975 | Jinotti |
| 3,903,883 A | | 9/1975 | Pecina et al. |
| 3,904,083 A | | 9/1975 | Little |
| 3,967,001 A | | 6/1976 | Almaula et al. |
| 3,987,941 A | | 10/1976 | Blessing |
| 3,993,246 A | | 11/1976 | Erb et al. |
| 4,042,153 A | | 8/1977 | Callahan et al. |
| 4,060,082 A | | 11/1977 | Lindberg et al. |
| 4,077,542 A | | 3/1978 | Petterson |

(List continued on next page.)

FOREIGN PATENT DOCUMENTS

| | | |
|---|---|---|
| BE | 354004 A | 9/1928 |
| BE | 354094 A | 9/1928 |
| DE | 1036470 B1 | 8/1958 |

(List continued on next page.)

OTHER PUBLICATIONS

Notification of Transmittal of the International Search Report or the Declaration for PCT/US02/38681 dated Apr. 1, 2003.

Barry, P.W. et al. "In Vitro Comparison of the Amount of Salbutamol Available for Inhalation From Different Formulations Used with Different Spacer Devices" Eur Respir J 1997; 10: 1345–1348.

(List continued on next page.)

*Primary Examiner*—Weilun Lo
*Assistant Examiner*—Michael Mendoza
(74) *Attorney, Agent, or Firm*—Burns, Doane, Swecker & Mathis, LLP

(57) ABSTRACT

An aerosol generator includes a heater arrangement having multiple heating sections and corresponding flow paths for volatilization of a fluid in liquid form. The flow paths can include first and second flow paths which are parallel to each other and sized such that the first flow path is smaller than the second flow path. During delivery of liquid to the flow paths, a smaller amount of vaporized liquid can be ejected from the first flow path, and the bulk of the vaporized liquid can be ejected from the second flow path.

33 Claims, 3 Drawing Sheets

U.S. PATENT DOCUMENTS

| | | |
|---|---|---|
| 4,161,282 A | 7/1979 | Erb et al. |
| 4,162,501 A | 7/1979 | Mitchell et al. |
| 4,215,708 A | 8/1980 | Bron |
| 4,231,492 A | 11/1980 | Rios |
| 4,258,073 A | 3/1981 | Payne |
| 4,261,356 A | 4/1981 | Turner et al. |
| 4,289,003 A | 9/1981 | Yang |
| 4,291,838 A | 9/1981 | Williams |
| 4,303,083 A | 12/1981 | Burruss, Jr. |
| 4,383,171 A | 5/1983 | Sinha et al. |
| 4,391,308 A | 7/1983 | Steiner |
| 4,395,303 A | 7/1983 | Weir |
| 4,433,797 A | 2/1984 | Galia |
| 4,471,892 A | 9/1984 | Coleman |
| 4,512,341 A | 4/1985 | Lester |
| 4,575,609 A | 3/1986 | Fassel et al. |
| 4,627,432 A | 12/1986 | Newell et al. |
| 4,649,911 A | 3/1987 | Knight et al. |
| 4,682,010 A * | 7/1987 | Drapeau et al. ............ 392/488 |
| 4,695,625 A | 9/1987 | Macdonald |
| 4,700,657 A | 10/1987 | Butland |
| 4,730,111 A | 3/1988 | Vestal et al. |
| 4,735,217 A * | 4/1988 | Gerth et al. ................ 131/273 |
| 4,744,932 A | 5/1988 | Browne |
| 4,749,778 A | 6/1988 | Fukuzawa et al. |
| 4,762,995 A | 8/1988 | Browner et al. |
| 4,776,515 A | 10/1988 | Michalchik |
| 4,790,305 A | 12/1988 | Zoltan et al. |
| 4,811,731 A | 3/1989 | Newell et al. |
| 4,819,625 A | 4/1989 | Howe |
| 4,819,834 A | 4/1989 | Thiel |
| 4,829,996 A | 5/1989 | Noakes et al. |
| 4,837,260 A | 6/1989 | Sato et al. |
| 4,848,374 A | 7/1989 | Chard et al. |
| 4,871,115 A | 10/1989 | Hessey |
| 4,871,623 A | 10/1989 | Hoopman et al. |
| 4,877,989 A | 10/1989 | Drews et al. |
| 4,911,157 A | 3/1990 | Miller |
| 4,922,901 A | 5/1990 | Brooks et al. |
| 4,926,852 A | 5/1990 | Zoltan et al. |
| 4,935,624 A | 6/1990 | Henion et al. |
| 4,941,483 A | 7/1990 | Ridings et al. |
| 4,947,875 A | 8/1990 | Brooks et al. |
| 4,974,754 A | 12/1990 | Wirz |
| 4,982,097 A | 1/1991 | Slivon et al. |
| 4,992,206 A | 2/1991 | Waldron |
| 5,021,802 A | 6/1991 | Allred |
| 5,044,565 A | 9/1991 | Alexander |
| 5,056,511 A | 10/1991 | Ronge |
| 5,060,671 A | 10/1991 | Counts et al. |
| 5,063,921 A | 11/1991 | Howe |
| 5,096,092 A | 3/1992 | Devine |
| 5,125,441 A | 6/1992 | Mette |
| 5,133,343 A | 7/1992 | Johnson, IV et al. |
| 5,134,993 A | 8/1992 | van der Linden et al. |
| 5,135,009 A | 8/1992 | Müller et al. |
| 5,144,962 A | 9/1992 | Counts et al. |
| 5,151,827 A | 9/1992 | Ven et al. |
| 5,178,305 A | 1/1993 | Keller |
| 5,184,776 A | 2/1993 | Minier |
| 5,217,004 A | 6/1993 | Blasnik et al. |
| 5,226,441 A | 7/1993 | Dunmire et al. |
| 5,228,444 A | 7/1993 | Burch |
| 5,230,445 A | 7/1993 | Rusnak |
| 5,231,983 A | 8/1993 | Matson et al. |
| 5,259,370 A | 11/1993 | Howe |
| 5,290,540 A | 3/1994 | Prince et al. |
| 5,298,744 A | 3/1994 | Mimura et al. |
| 5,299,565 A | 4/1994 | Brown |
| 5,322,057 A | 6/1994 | Raabe et al. |
| 5,327,915 A * | 7/1994 | Porenski et al. ............ 131/194 |
| 5,342,180 A | 8/1994 | Daoud |
| 5,342,645 A | 8/1994 | Eisele et al. |
| 5,349,946 A | 9/1994 | McComb |
| 5,395,445 A | 3/1995 | Bohanan |
| 5,421,489 A | 6/1995 | Holzner, Sr. et al. |
| 5,462,597 A | 10/1995 | Jubran |
| 5,474,059 A | 12/1995 | Cooper |
| 5,515,842 A | 5/1996 | Ramseyer et al. |
| 5,522,385 A | 6/1996 | Lloyd et al. |
| 5,556,964 A | 9/1996 | Hofstraat et al. |
| 5,564,442 A | 10/1996 | MacDonald et al. |
| 5,565,677 A | 10/1996 | Wexler |
| 5,575,929 A | 11/1996 | Yu et al. |
| 5,585,045 A | 12/1996 | Heinonen et al. |
| 5,617,844 A | 4/1997 | King |
| 5,642,728 A | 7/1997 | Andersson et al. |
| 5,674,860 A | 10/1997 | Carling et al. |
| 5,682,874 A | 11/1997 | Grabenkort et al. |
| 5,730,158 A | 3/1998 | Collins et al. |
| 5,743,251 A * | 4/1998 | Howell et al. ......... 128/200.14 |
| 5,756,995 A | 5/1998 | Maswadeh et al. |
| 5,765,724 A | 6/1998 | Amberg et al. |
| 5,823,178 A | 10/1998 | Lloyd et al. |
| 5,839,430 A | 11/1998 | Cama |
| 5,855,202 A | 1/1999 | Andrade |
| 5,856,671 A | 1/1999 | Henion et al. |
| 5,863,652 A | 1/1999 | Matsumura et al. |
| 5,869,133 A | 2/1999 | Anthony et al. |
| 5,872,010 A | 2/1999 | Karger et al. |
| 5,878,752 A | 3/1999 | Adams et al. |
| 5,881,714 A | 3/1999 | Yokoi et al. |
| 5,906,202 A | 5/1999 | Schuster et al. |
| 5,914,122 A | 6/1999 | Otterbeck et al. |
| 5,932,249 A | 8/1999 | Gruber et al. |
| 5,932,315 A | 8/1999 | Lum et al. |
| 5,934,272 A | 8/1999 | Lloyd et al. |
| 5,934,273 A | 8/1999 | Andersson et al. |
| 5,944,025 A | 8/1999 | Cook et al. |
| 5,951,923 A * | 9/1999 | Horie et al. ................ 261/153 |
| 5,954,979 A | 9/1999 | Counts et al. |
| 5,957,124 A | 9/1999 | Lloyd et al. |
| 5,970,973 A | 10/1999 | Gonda et al. |
| 5,970,974 A | 10/1999 | Van Der Linden et al. |
| 5,978,548 A | 11/1999 | Holmstrand et al. |
| 5,993,633 A | 11/1999 | Smith et al. |
| 6,014,970 A | 1/2000 | Ivri et al. |
| 6,053,176 A | 4/2000 | Adams et al. |
| 6,054,032 A | 4/2000 | Haddad et al. |
| 6,069,214 A | 5/2000 | McCormick et al. |
| 6,069,219 A | 5/2000 | McCormick et al. |
| 6,070,575 A | 6/2000 | Gonda et al. |
| 6,071,428 A | 6/2000 | Franks et al. |
| 6,076,522 A | 6/2000 | Dwivedi et al. |
| 6,077,543 A | 6/2000 | Gordon et al. |
| 6,080,721 A | 6/2000 | Patton |
| 6,085,740 A | 7/2000 | Ivri et al. |
| 6,085,753 A | 7/2000 | Gonda et al. |
| 6,089,228 A | 7/2000 | Smith et al. |
| 6,095,153 A * | 8/2000 | Kessler et al. .............. 131/194 |
| 6,098,615 A | 8/2000 | Lloyd et al. |
| 6,098,620 A | 8/2000 | Lloyd et al. |
| 6,103,270 A | 8/2000 | Johnson et al. |
| 6,116,516 A | 9/2000 | Gañán-Calvo |
| 6,116,893 A | 9/2000 | Peach |
| 6,119,953 A | 9/2000 | Gañán-Calvo et al. |
| 6,123,068 A | 9/2000 | Lloyd et al. |
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |

| | | | |
|---|---|---|---|
| 6,138,668 A | 10/2000 | Patton et al. | |
| 6,155,268 A * | 12/2000 | Takeuchi | |
| 6,158,431 A | 12/2000 | Poole | |
| 6,158,676 A | 12/2000 | Hughes | |
| 6,159,188 A | 12/2000 | Laibovitz et al. | |
| 6,164,630 A | 12/2000 | Birdsell et al. | |
| 6,165,463 A | 12/2000 | Platz et al. | |
| 6,167,880 B1 | 1/2001 | Gonda et al. | |
| 6,174,469 B1 | 1/2001 | Gañán-Calvo | |
| 6,182,712 B1 | 2/2001 | Stout et al. | |
| 6,187,214 B1 | 2/2001 | Gañán-Calvo | |
| 6,187,344 B1 | 2/2001 | Eljamal et al. | |
| 6,189,803 B1 | 2/2001 | Gañán-Calvo | |
| 6,192,882 B1 | 2/2001 | Gonda | |
| 6,197,835 B1 | 3/2001 | Gañán-Calvo | |
| 6,205,999 B1 | 3/2001 | Ivri et al. | |
| 6,206,242 B1 | 3/2001 | Amberg et al. | |
| 6,207,135 B1 | 3/2001 | Rössling et al. | |
| 6,223,746 B1 | 5/2001 | Jewett et al. | |
| 6,230,706 B1 | 5/2001 | Gonda et al. | |
| 6,231,851 B1 | 5/2001 | Platz et al. | |
| 6,234,167 B1 * | 5/2001 | Cox et al. | 128/200.14 |
| 6,234,402 B1 | 5/2001 | Gañán-Calvo | |
| 6,235,177 B1 | 5/2001 | Borland et al. | |
| 6,250,298 B1 | 6/2001 | Gonda et al. | |
| 6,257,233 B1 | 7/2001 | Burr et al. | |
| 6,258,341 B1 | 7/2001 | Foster et al. | |
| 6,263,872 B1 | 7/2001 | Schuster et al. | |
| 6,267,155 B1 | 7/2001 | Parks et al. | |
| 6,275,650 B1 | 8/2001 | Lambert | |
| 6,276,347 B1 | 8/2001 | Hunt | |
| 6,284,525 B1 | 9/2001 | Mathies et al. | |
| 6,288,360 B1 | 9/2001 | Beste | |
| 6,290,685 B1 | 9/2001 | Insley et al. | |
| 6,294,204 B1 | 9/2001 | Rössling et al. | |
| 6,295,986 B1 | 10/2001 | Patel et al. | |
| 6,318,361 B1 | 11/2001 | Sosiak | |
| 6,390,453 B1 * | 5/2002 | Frederickson et al. | 261/26 |
| 2001/0032647 A1 | 10/2001 | Schuster et al. | |

FOREIGN PATENT DOCUMENTS

| | | |
|---|---|---|
| EP | 0358114 A | 3/1990 |
| EP | 0642802 A2 | 5/1996 |
| FR | 667979 A | 10/1929 |
| HU | 168128 B | 11/1977 |
| HU | 216121 B | 3/1991 |
| HU | 207457 A | 4/1993 |
| HU | P953409 | 6/1994 |
| WO | 94/09842 A | 5/1994 |
| WO | 98/17131 | 4/1998 |
| WO | 00/21598 | 4/2000 |

OTHER PUBLICATIONS

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477–7505, May–Jun. 1994 (023).

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp. 97–102.

Hou, Shuguang et al. *Solution Stability of Budenosonide in Novel Aerosol Formulations* Abstract No. 2582, Solid State Physical Pharmacy, Nov. 17, 1998, p. S–307.

Kousaka, Yasuo et al., "Generation of Aerosol Particles by Boiling of Suspensions", Aerosol Science and Technology, 21:236–240 (1994) (023).

Morén, Folke "Drug Deposition of Pressurized Inhalation Aerosols I. Influence of Actuator Tube Design" AB Draco (Subsidiary of AB Astra, Sweden) Research and Development Laboratories Pack, S–221 01 Lund (Sweden), International Journal of Pharmaceutrics, 1 (1978) 205–212.

Newman, Stephen P. et al. "Deposition of Pressurized Suspension Aerosols Inhaled Through Extension Devices[1–3]" Am Rev Respir Dis 1981; 124:317–320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766–770, Jul. 1980.

* cited by examiner

AEROSOL GENERATOR HAVING A MULTIPLE PATH HEATER ARRANGEMENT AND METHOD OF USE THEREOF

BACKGROUND OF THE INVENTION

1. Field of the Invention

The present invention relates generally to aerosol generators and, more particularly, to aerosol generators which include a heater for volatilizing liquid material. The present invention also relates to methods for generating an aerosol. The present invention has particular applicability to the generation of aerosols containing medicated material.

2. Description of the Related Art

Aerosols are gaseous suspensions of fine solid or liquid particles and are useful in a wide variety of applications. For example, medicated liquids and powders may be administered in aerosol form. Such medicated aerosols include, for example, materials which are useful in the treatment of respiratory ailments, in which case the aerosols may be inhaled into a patient's lungs. Aerosols may also be used in non-medicinal applications including, for example, dispensing air fresheners and insecticides and delivering paints and/or lubricants.

In aerosol inhalation applications, it is typically desirable to provide an aerosol having an average mass median particle diameter of less than 2 microns to facilitate deep lung penetration. Most known aerosol generators are incapable of generating aerosols having an average mass median particle diameter less than 2 microns. Also, in certain applications, it is generally desirable to deliver medicated material at high flow rates, for example, above 1 mg per second. Most known aerosol generators suited for delivering medicated material are incapable of delivering material at such high flow rates while maintaining a suitable average mass median particle diameter. In addition, most known aerosol generators deliver an imprecise amount of aerosol compared with the amount of aerosol that is intended to be delivered.

Commonly owned U.S. Pat. Nos. 5,743,251 and 6,234,167, disclose aerosol generators designed for volatilizing a liquid and ejecting the volatilized liquid into the atmosphere. The volatilized liquid subsequently condenses, thereby forming an aerosol. Such aerosol generators may utilize resistance heating materials to volatilize the liquid. However, generators having a single zone wherein the liquid is heated may not provide optimal delivery of the volatilized liquid.

In light of the foregoing, there exists a need in the art for the provision of an aerosol generator which provides improved aerosol delivery of volatilized liquid.

SUMMARY OF THE INVENTION

According to a first aspect of the present invention, an aerosol generator includes a liquid supply, a flow passage having at least one inlet that is in fluid communication with the liquid supply, the flow passage including at least first and second flow paths and at least one outlet, and a heater arrangement including first and second heating sections, the first heating section being adapted to heat liquid in the first flow path sufficiently to vaporize the liquid so as to form a vaporized liquid ejected from the at least one outlet, and the second heating section being adapted to heat liquid in the second flow path sufficiently to vaporize liquid so as to form a vaporized liquid ejected from the at least one outlet.

The invention also provides a method for generating an aerosol using an aerosol generator comprising (1) a flow passage having an inlet in fluid communication with a liquid supply, the flow passage including at least first and second flow paths and at least one outlet; and (2) a multi-path heater arranged to volatilize fluid, wherein the heater includes at least first and second heating sections, the first heating section being adapted to heat liquid in the first flow path sufficiently to vaporize the liquid so as to form a vaporized liquid ejected from the at least one outlet, and a second heating section being adapted to heat liquid in the second flow path sufficiently to vaporize the liquid so as to form a vaporized liquid ejected from the at least one outlet, the method comprising activating the heater arrangement of the aerosol generator to provide a differential heating rate in the first and second flow passages, and directing a smaller amount of volatilized fluid out of the first flow path, prior to directing the bulk of volatilized fluid out of the second flow path.

BRIEF DESCRIPTION OF THE DRAWINGS

The objects and advantages of the invention will become apparent from the following detailed description of the preferred embodiments thereof in connection with the accompanying drawings, in which.

DETAILED DESCRIPTION OF THE PREFERRED EMBODIMENTS OF THE INVENTION

Figure 1:
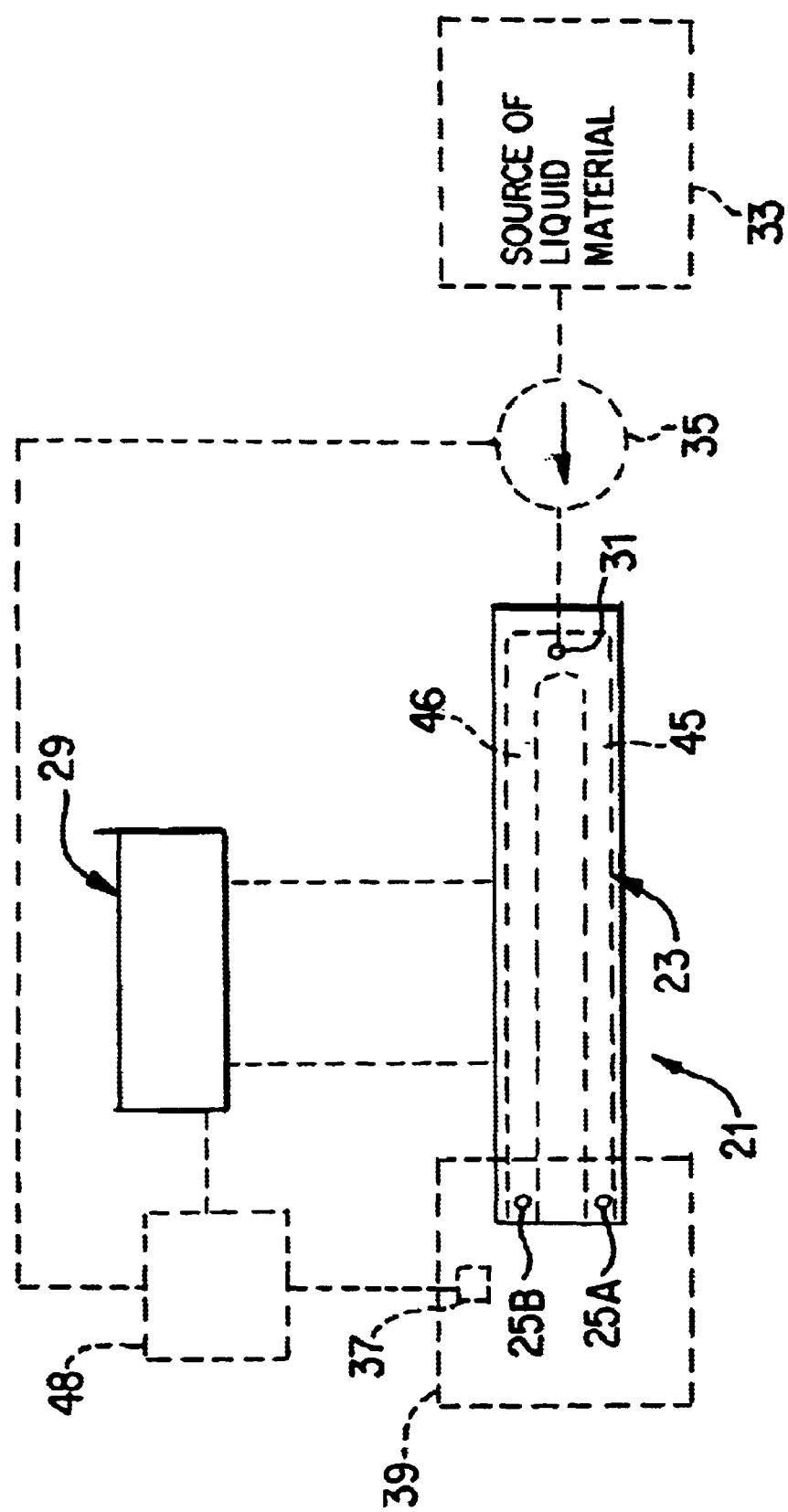
FIG. 1 is a schematic view of an aerosol generator of an inhaler according to a first embodiment of the present invention.

The present invention provides improvements in delivery of volatilized liquid from an aerosol generator via a multi-path heating arrangement which can deliver low volume mass per inhalation cycle, volatilize low solute containing solutions, minimize overheating, minimize power requirements, form volatilized liquid more quickly and/or form a predetermined amount of aerosol in a shorter time than in aerosol generators utilizing a single flow passage/heater arrangement. The invention is described with reference to embodiments shown in the drawing figures, wherein like reference numerals designate identical or corresponding elements throughout the several figures.

An aerosol generator 21 of an inhaler according to a first embodiment of the present invention is shown with reference to FIG. 1. The aerosol generator 21 includes a liquid supply 33 which is in direct communication with a multiple path heater arrangement 23. The heater arrangement 23 is connected to a power supply 29, preferably a DC power source such as a battery. Liquid from liquid source 33 is delivered to flow paths 45 and 46, by any suitable arrangement such as a syringe pump, pressurized container, valve arrangement or the like. In the embodiment shown, a valve 35 is used to deliver a predetermined amount of liquid to inlet 31 of a flow passage which branches into flow paths 45,46. Activation of the valve can be controlled by a controller 48 upon receiving a signal from an optional puff activated sensor 37. The controller also activates heater arrangement 23 by supplying power from power supply 29 whereby vaporized liquid is ejected from outlets 25A,25B and/or aerosol is formed in optional mouth piece 39 for inhalation by a user of the device. If desired, a single outlet may be used in lieu of the two outlet arrangement.

Figure 2:
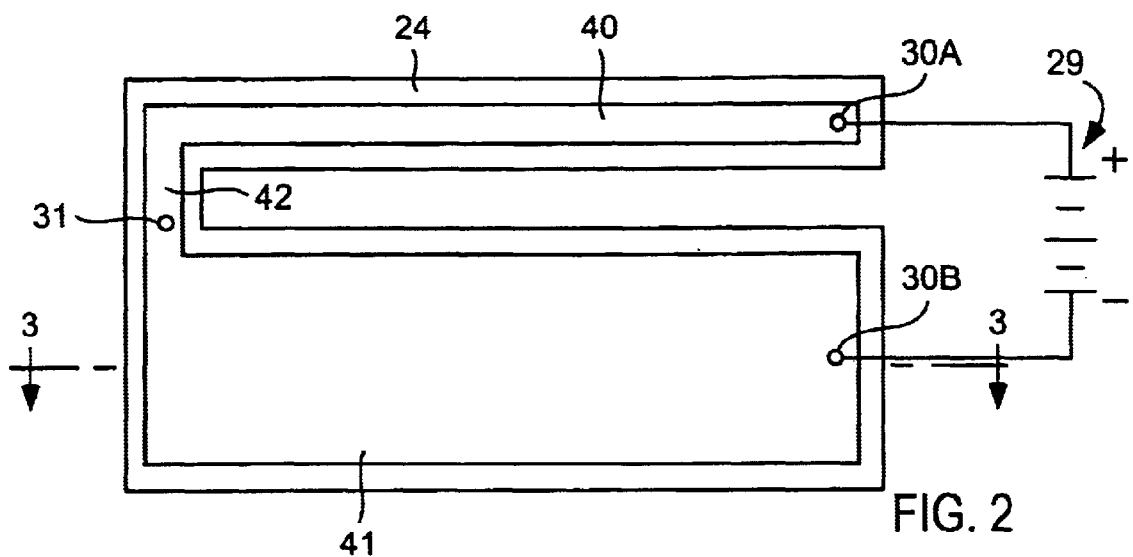
FIG. 2 is a top plan view of a base plate of a multiple path heater arrangement according to the present invention.
Figure 3:
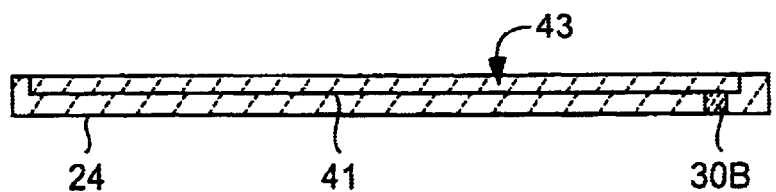
FIG. 3 is a side sectional view along line A—A of a base plate according to the present invention.
Figure 4:
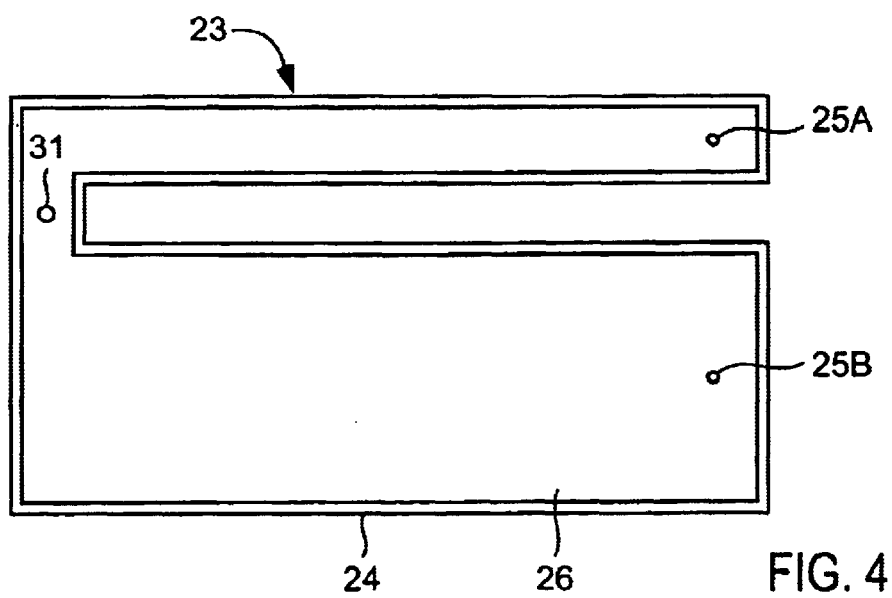
FIG. 4 is a top plan view of an assembled multiple path heater arrangement according to an embodiment of the present invention.
Figure 5:
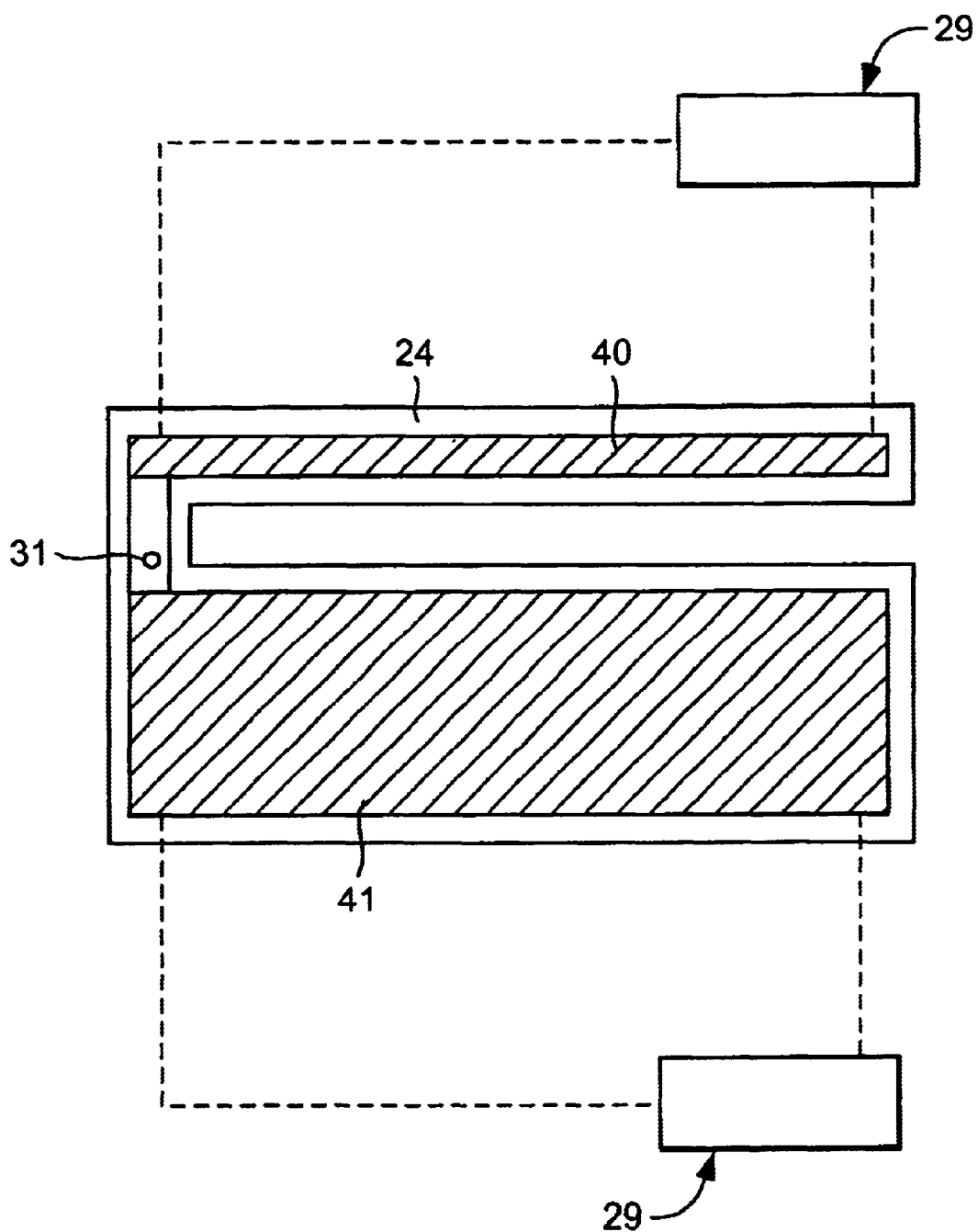
FIG. 5 is a top plan view of a base plate of a multiple path heater arrangement according to another preferred embodiment.

FIGS. 2–4 show a multi-path heater arrangement according to a preferred embodiment of the invention wherein FIG. 2 shows a top view of a base plate 24, FIG. 3 shows a side view of the base plate 24, and FIG. 4 shows a top view of a top plate 26 assembled to the base plate. The base plate 24 and top plate 26 when assembled form the multilayered composite heater arrangement 23 shown in FIG. 1.

The aerosol generator 21 can produce an aerosol from a fluid in liquid form by volatilizing the fluid at a differential heating rate within the flow paths 45 and 46. The flow paths 45, 46 can have any desired configuration. For example, flow path 45 can comprise a straight and uniform cross-sectioned channel which is parallel to flow path 46 as shown in FIG. 1. However, the flow paths could have non-uniform cross-sections, could be non-parallel and/or could be non-linear flow paths.

FIG. 2 shows an arrangement wherein the multiple path heater comprises at least two heating zones 40,41. The first heating zone 40 is located along the first flow path 45 which preferably has a smaller cross-sectional area than the second flow path 46. The smaller cross-sectional area of the first flow path 45 allows for faster heating of the fluid which passes through the heater arrangement 23. As such, when the volatilized fluid enters through the liquid inlet hole 31 and flows through the first and second flow paths 45 and 46, a preliminary amount of volatilized fluid will be produced within the smaller cross-sectional area defined by the first flow path 45 and delivered to outlet 25A, prior to volatilization of fluid in the second flow path 46. Thus, the aerosol generator can deliver an aerosol to a user of the device within a short time of actuation of the heater. While the preliminary amount of volatilized fluid is formed, the second heating section can heat sufficiently to deliver a bulk amount of volatilized fluid to outlet 25B. The first heating zone 40 and second heating zone 41 can have the same or different thermal masses.

The flow paths 45, 46 can be formed in a ceramic or polymer base plate 24 by molding, machining or other suitable technique. For example, the base plate 24 can be a green ceramic tape of alumina and the flow paths can be press formed into the ceramic tape. Alternatively, the base plate 24 can be a sintered ceramic plate and the flow paths 45, 46 can be laser machined into the plate. The flow paths can have any desired configuration and/or dimensions in terms of length, width and depth. For example, the flow paths 45, 46 can be parallel to each other with capillary dimensions, e.g., a depth of 0.01 to 10 mm, preferably 0.05 to 1 mm, and more preferably about 0.1 to 0.5 mm with the width and length of the flow path being any suitable dimensions, e.g., width of 1 mm or more and length of 10 mm or more. The width of flow path 46 is preferably 2 to 10 times greater than that of flow path 45, e.g., flow path 46 can be around 4 times wider than flow path 45. Alternatively, the smaller capillary passage can be defined by transverse cross sectional area of the passage which can be $8\times10^{-5}$ to 80 $mm^2$, preferably $2\times10^{-3}$ to $8\times10^{-1}$ $mm^2$ and more preferably $8\times10^{-3}$ to $2\times10^{-1}$ $mm^2$.

The power supply 29 is preferably battery operated by a controller and connected to the multiple path heater arrangement 23 via electrical feedthroughs 30A and 30B. This will allow for a continuous electrical circuit within the multiple path heater and faster heating of the heating zone 40 due to its smaller cross section. The heating zones 40,41 and optional intermediate section 42 can comprise a coating of resistance heating material located in flow paths 45,46. For example, a resistance heating material such as platinum can be deposited such as by sputtering on surfaces of the base plate 24 defining the flow paths 45,46. However, the heater can comprise a layer or layers of heating material on outer surfaces of top and/or bottom plates 24,26. Liquid from a fluid supply can be supplied continuously or intermittently to inlet hole 31. For inhaler devices, the inlet hole can have a size of 0.05 to 5 mm, preferably 0.1 to 1 mm. As the liquid enters into the fluid inlet hole 31, the continuous electrical circuit allows for the heating of the heating zones 41,42 within fluid channel 43 as indicated in FIG. 3. Heating zones 40,41 can be interconnected by intermediate zone 42 in the case where the heating zones 40,41 are formed from a continuous layer of resistance heating material. However, the heating zones 40,41 could be formed from discrete sections of heater material in which case separate electrical connections would be attached to each heater section. FIG. 5 illustrates an embodiment of the aerosol generator including two power sources 29, which power the first heating zone 40 independently of the second heating zone 41.

FIG. 4 shows a top plate 26 assembled on the base plate 24. The top and base plates can be held together with a suitable adhesive such as cement, epoxy, metallized glass, brazing material or the like. The heater arrangement 23, which includes first and second heating sections 40 and 41, is adapted to heat liquids in a first flow path 45 sufficiently to vaporize the liquid so as to form a vaporized liquid ejected from the first outlet 25A. The second heating section 41 is adapted to heat liquid in the second flow path 46 sufficiently to vaporize the liquid so as to form a vaporized liquid ejected from the second outlet 25B. For inhaler devices, the outlets 25A and 25B can be round holes having a diameter of 0.05 to 5 mm, preferably 0.1 to 1 mm. This arrangement allows for rapid heating of the liquid in the first flow path 45.

While the invention has been described in detail with reference to preferred embodiments, it will be apparent to one skilled in the art that various changes can be made, and equivalents employed, without departing from the scope of the invention.

What is claimed is:

1. An aerosol generator useful for generating vaporized fluid comprising:

a liquid supply;

a flow passage having at least one inlet in fluid communication with the liquid supply, the flow passage including at least first and second flow paths and at least one outlet;

a heater arrangement including first and second heating sections, the first heating section being adapted to heat liquid in the first flow path sufficiently to vaporize the liquid so as to form a vaporized liquid ejected from the at least one outlet, and the second heating section being adapted to heat liquid in the second flow path sufficiently to vaporize the liquid so as to form a vaporized liquid ejected from the at least one outlet.

2. The aerosol generator of claim 1, wherein the heater arrangement comprises at least one layer of resistance heating material and/or the at least first and second flow paths have capillary dimensions.

3. The aerosol generator of claim 2, wherein the first and second heating sections have the same or different electrical resistance.

4. The aerosol generator of claim 2, wherein the resistance heating material comprises a platinum coating.

5. The aerosol generator of claim 2, wherein the heater arrangement includes an intermediate section of resistance heating material extending between the first and second heating sections.

6. The aerosol generator of claim 2, wherein the first heating section is powered independently from the second heating section.

7. The aerosol generator of claim 2, wherein the first and second heating sections are powered by a single electrical power source.

8. The aerosol generator of claim 1, wherein the at least one outlet comprises first and second outlets.

9. The aerosol generator of claim 1, further comprising a controller, valve and a sensor, the sensor detecting a delivery condition corresponding to delivery of a predetermined volume of aerosol, the controller being programmed to open the valve so as to deliver liquid to the first and second flow paths when the delivery condition is sensed by the sensor and to activate the heating sections to volatilize liquid in the first and second flow paths.

10. The aerosol generator of claim 1, wherein the first heating section is thermally isolated from the second heating section.

11. The aerosol generator of claim 1, wherein the first heating section is thermally integrated with the second heating section.

12. The aerosol generator of claim 1, wherein the first and second heating sections have the same or different thermal masses.

13. The aerosol generator of claim 1, further comprising a mouthpiece of an inhaler, the at least one outlet being located inside the mouthpiece so as to form an aerosol within the mouthpiece when volatilized liquid material is ejected from the at least one outlet.

14. The aerosol generator of claim 1, wherein the first and second flow paths are in fluid connection at upstream ends thereof and the at least one inlet consists of a single inlet supplying liquid to the first and second flow paths.

15. The aerosol generator of claim 1, wherein the first and second heating sections comprise planar strips of electrically resistive heating material.

16. The aerosol generator of claim 1, wherein the first and second flow paths comprise first and second channels in a ceramic substrate.

17. The aerosol generator of claim 16, wherein the first and second channels being less than or equal to 10 mm in depth.

18. The aerosol generator of claim 16, wherein the first and second heating sections comprise resistance heating material in the channels.

19. The aerosol generator of claim 18, wherein at least one electrical feedthrough extends through the ceramic substrate and supplies power to the heating sections.

20. The aerosol generator of claim 19, wherein the at least one feedthrough comprises a first feedthrough connected to a downstream end of the first heating section and a second feedthrough connected to a downstream end of the second heating section.

21. An aerosol generator useful for generating vaporized fluid, comprising:

a base plate;

a cover plate;

a flow passage having at least one inlet adapted to receive liquid from a liquid supply, the flow passage including at least first and second flow paths between the base plate and the cover plate and including at least one outlet;

a heater arrangement including first and second heating sections, the first heating section being adapted to heat liquid in the first flow path sufficiently to vaporize the liquid so as to form a vaporized liquid ejected from the at least one outlet, and the second heating section being adapted to heat liquid in the second flow path sufficiently to vaporize the liquid so as to form a vaporized liquid ejected from the at least one outlet.

22. The aerosol generator of claim 21, wherein the first heating section comprises a layer of resistance heating material in the first channel and the second heating section comprises a layer of resistance heating material in the second channel.

23. An aerosol generator useful for generating vaporized fluid, comprising:

a flow passage having at least one inlet adapted to receive liquid from a liquid supply, the flow passage including at least first and second flow paths and at least one outlet; and a heater arrangement including first and second heating sections, the first and second heating sections comprising planar strips of electrically resistive heating material which are parallel to each other, the first heating section being adapted to heat liquid in the first flow path sufficiently to vaporize the liquid so as to form a vaporized liquid ejected from the at least one outlet, and the second heating section being adapted to heat liquid in the second flow path sufficiently to vaporize the liquid so as to form a vaporized liquid ejected from the at least one outlet.

24. The aerosol generator of claim 23, wherein the first and second heating sections are interconnected by an intermediate section comprising a planar strip of electrically resistive heating material.

25. A method for generating an aerosol, comprising:

(a) supplying a material in liquid form to an inlet of an aerosol generator having a flow passage which includes first and second flow paths, the first flow path being smaller in size than the second flow path; and (b) heating the liquid in the first and second flow paths to a temperature sufficient to volatilize the liquid and eject volatilized liquid from at least one outlet, the heating being carried out by energizing first and second heating sections, the liquid in the first flow path being volatilized by the first heating section before the liquid in the second flow path is volatilized by the second heating section.

26. The method of claim 25, wherein the aerosol generator includes a controller, a valve and a sensor, the method including:

sensing a delivery condition with the sensor;

sending a signal to the controller corresponding to detection of the delivery condition;

opening the valve for delivery of a predetermined volume of liquid to the first and second flow paths when the controller receives the signal;

supplying power to first and second heating sections which heat the liquid in the first and second flow paths; and closing the valve when the predetermined volume of fluid has been delivered to the first and second flow paths.

27. An aerosol generator useful for generating vaporized fluid, comprising:

a flow passage having at least one inlet adapted to receive liquid from a liquid supply, the flow passage including at least first and second flow paths and at least one outlet; and a heater arrangement including first and second heating sections, the first heating section being adapted to heat liquid in the first flow path sufficiently to vaporize the liquid so as to form a vaporized liquid ejected from the at least one outlet, and the second heating section being adapted to heat liquid in the second flow path sufficiently to vaporize the liquid so as to form a vaporized liquid ejected from the at least one outlet;

wherein the first heating section volatilizes liquid in the first flow path faster than the second heating section volatilizes liquid in the second flow path when liquid is supplied to the first and second flow paths.

28. An aerosol generator useful for generating vaporized fluid, comprising:

a flow passage having at least one inlet adapted to receive liquid from a liquid supply, the flow passage including at least first and second flow paths and at least one outlet, the first flow path being sized to hold less than one-half an amount of liquid contained in the second flow path; and a heater arrangement including first and second heating sections, the first heating section being adapted to heat liquid in the first flow path sufficiently to vaporize the liquid so as to form a vaporized liquid ejected from the at least one outlet, and the second heating section being adapted to heat liquid in the second flow path sufficiently to vaporize the liquid so as to form a vaporized liquid ejected from the at least one outlet.

29. An aerosol generator useful for generating vaporized fluid, comprising:

a flow passage having at least one inlet adapted to receive liquid from a liquid supply, the flow passage including at least first and second flow paths and at least one outlet; and a heater arrangement including first and second heating sections, the first heating section being adapted to heat liquid in the first flow path sufficiently to vaporize the liquid so as to form a vaporized liquid ejected from the at least one outlet, and the second heating section being adapted to heat liquid in the second flow path sufficiently to vaporize the liquid so as to form a vaporized liquid ejected from the at least one outlet, the first and second heating sections ejecting different volumes of vaporized liquid from the at least one outlet during delivery of a fixed volume of liquid to the flow passage.

30. An aerosol generator useful for generating vaporized fluid, comprising:

a flow passage having at least one inlet adapted to receive liquid from a liquid supply, the flow passage including at least first and second flow paths and at least one outlet; and a heater arrangement including first and second heating sections, the first heating section having a different cross-sectional area than the second heating section, the first heating section being adapted to heat liquid in the first flow path sufficiently to vaporize the liquid so as to form a vaporized liquid ejected from the at least one outlet, and the second heating section being adapted to heat liquid in the second flow path sufficiently to vaporize the liquid so as to form a vaporized liquid ejected from the at least one outlet.

31. A method for generating an aerosol, comprising steps of:

(a) supplying a material in liquid form to an inlet of an aerosol generator having a flow passage which includes first and second flow paths; and (b) heating the liquid in the first and second flow paths to a temperature sufficient to volatilize the liquid and eject volatilized liquid from at least one outlet.

32. A method for generating an aerosol, comprising:

(a) supplying a material in liquid form to an inlet of an aerosol generator having a flow passage which includes first and second flow paths; and (b) heating the liquid in the first and second flow paths to a temperature sufficient to volatilize the liquid and eject a first amount of the volatilized liquid from a first outlet and eject a second amount of volatilized liquid from a second outlet, the first amount being smaller than the second amount.

33. A heater arrangement useful for vaporizing liquid, comprising:

a heater arrangement including first and second heating sections, the first heating section being disposed along a first flow path of a flow passage and being adapted to heat liquid in the first flow path sufficiently to vaporize the liquid so as to form a vaporized liquid ejected from at least one outlet of the flow passage, and the second heating section being disposed along a second flow path of the flow passage and adapted to heat liquid in the second flow path sufficiently to vaporize the liquid so as to form a vaporized liquid ejected from the at least one outlet;

wherein the first heating section volatilizes liquid in the first flow path faster than the second heating section volatilizes liquid in the second flow path when liquid is supplied to the first and second flow paths.

* * * * *